United States Patent [19]

Yang et al.

[11] Patent Number: 5,034,499

[45] Date of Patent: Jul. 23, 1991

[54] ACETAL COPOLYMERS WITH BACKBONE EPOXIDE FUNCTIONAL GROUPS

[75] Inventors: Nan-Loh Yang, Staten Island, N.Y.; Andrew Auerbach, Livingston; James L. Paul, Summit, both of N.J.; Yong C. Zheng; Shian S. Wang, both of New York, N.Y.

[73] Assignee: Hoechst Celanese Corp., Short Hills, N.J.

[21] Appl. No.: 181,233

[22] Filed: Apr. 13, 1988

[51] Int. Cl.$^5$ .............................................. C08G 2/22
[52] U.S. Cl. ..................................... 528/250; 528/248
[58] Field of Search ................................ 528/248, 250

[56] References Cited

U.S. PATENT DOCUMENTS

| | | |
|---|---|---|
| 3,297,647 | 1/1967 | Schott et al. |
| 3,337,587 | 8/1967 | Tinsley, Jr. et al. |
| 3,385,832 | 5/1968 | Jenning et al. ....................... 528/246 |

FOREIGN PATENT DOCUMENTS

| | | |
|---|---|---|
| 720516 | 10/1965 | Canada . |
| 1196374 | 7/1965 | Fed. Rep. of Germany . |
| 2062958 | 7/1971 | Fed. Rep. of Germany . |
| 837464 | 6/1960 | United Kingdom . |

OTHER PUBLICATIONS

R. C. Schulz, Makromol. Chem. Suppl. 12, 1-9 (1985).
R. C. Schulz, Makromol. Chem. Suppl. 13, 123-136 (1985).
W. Hellerman and R. C. Schulz, Makromol. Chem., Rapid Commun. 2, 585-589 (1981).
K. C. Brannock and G. R. Lappin, J. Organic Chem. 21, 1366-1368 (1956).
L. Berchenbach and M. Linhard, Ber., 64, 1081-1087 (1931).
A. M. Partansky, Epoxy Resins, Adv. Chem. Ser., 92, 29-47 (1970).
P. H. Plesch and P. H. Westermann, Polymer, 10:105 (1965).
E. J. Vandenberg, J. of Polymer Sci., Polymer Chem. Ed., 23, 951-970 (1985).
J. G. Dorsey, G. F. Dorsey, A. C. Rutenberg and L. A. Green, Analytical Chem. 49, 1144-1145 (1977).
S. Penszek et al., Adv. Polymer Sci. 68/69, Cationic Ring Opening Polymerization, 2, Synthetic Applications, p. 91 (1981).

*Primary Examiner*—Melvyn I. Marquis
*Assistant Examiner*—R. Dean, Jr.
*Attorney, Agent, or Firm*—White & Case

[57] ABSTRACT

Acetal copolymers of trioxane with epoxy functional groups are obtained by copolymerizing trioxane with 5,6-epoxy-1,3-dioxepane. The epoxide group in the polymer chain provides a highly reacting functional group for further modification. Acetal copolymers with backbone epoxide groups exhibit toughness and thermal stability. The backbone epoxide groups can also be aminated in a one step hydrolysis-amination process.

2 Claims, 2 Drawing Sheets

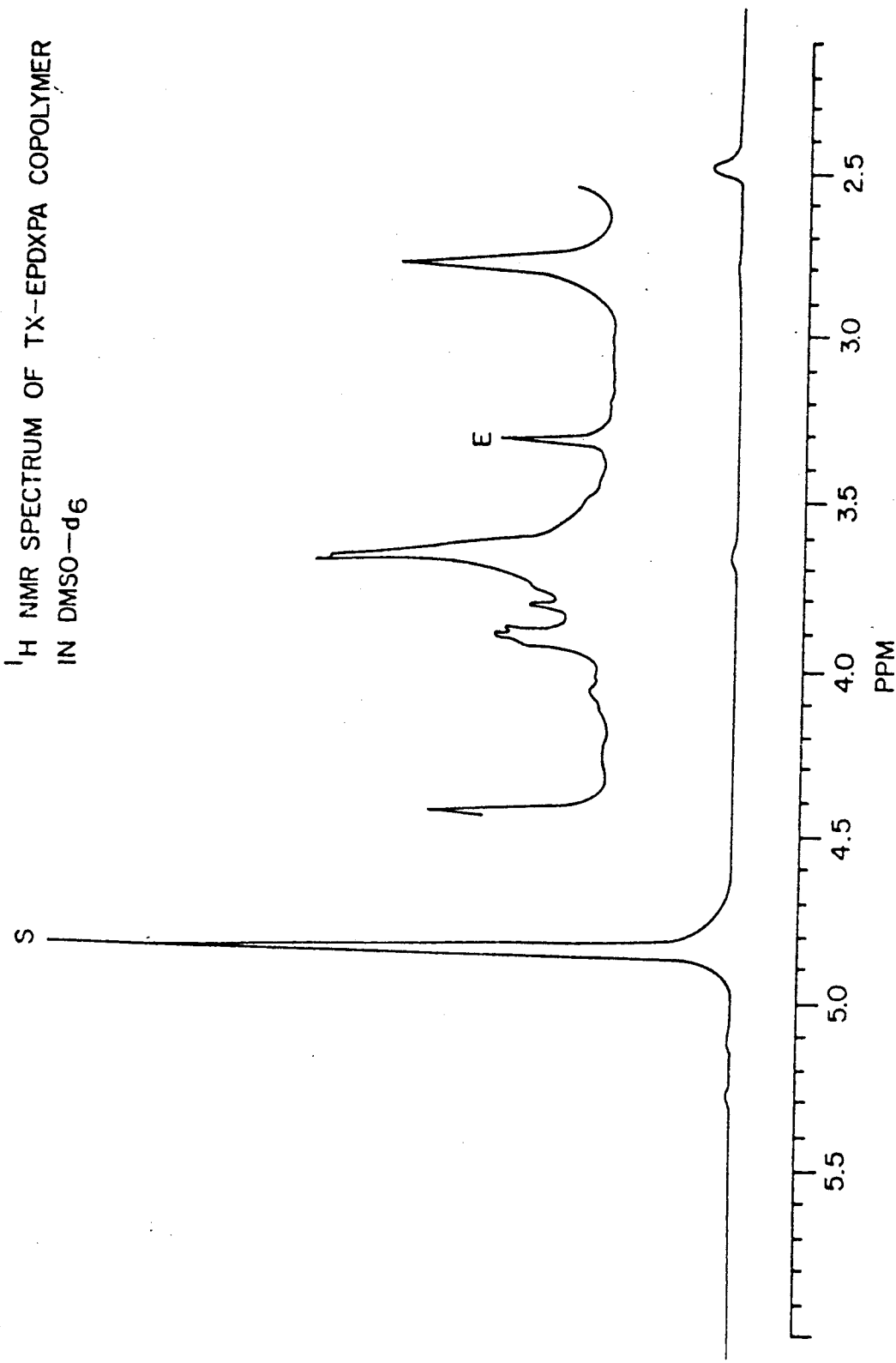

ACETAL COPOLYMERS WITH BACKBONE EPOXIDE FUNCTIONAL GROUPS

BACKGROUND OF THE INVENTION

Polyacetal copolymers are technically important macromolecules competitive with metals, ceramics and nylons in many applications. In the current technical processes, they are prepared by copolymerization of trioxane, with a comonomer such as ethylene oxide, dioxolane or butanediol formal. Each such copolymer molecule carries a maximum of two functional groups, e.g. hydroxyl end groups. For purposes such as preparation of graft copolymers and polymers with chemically bound stabilizers, it is desirable to synthesize polyacetals with higher levels of functional groups. It is an object of this invention to prepare polyacetal copolymers of trioxane that have stability equivalent to or greater than that of commercially available acetal copolymer while at the same time having functional groups which may be useful for further modifications or the attachment of additives.

In conventional acetal resin products, additives such as amidine thermal stabilizers and the like tend to reside in the amorphous regions of the polymer. Since the distribution of such non-crystalline areas is spatially random, the distribution of additives is often not optimal in terms of macroscopic properties. If functional sites can be provided at regular or semi-regular intervals (e.g. random copolymer) such that stabilizers or impact modifiers could be attached at a predetermined locus of points within the resin, then superior and more uniform properties could be achieved. This approach may be particularly advantageous since the crystal structure of acetal is such that additives are sterically obstructed from the crystalline areas. It therefore may be desirable to provide polymer backbone moieties that may disrupt the polymer's crystal structure in a controlled manner and provide a locus for attachment of additives.

Polyacetal copolymers with such backbone functional groups would be useful in many important applications such as: (a) preparing trioxane copolymers with chemically bonded stabilizers; (b) preparing trioxane copolymers with chemically attached impact modifiers; (c) preparing grafted copolymers of trioxane as compatibilizers with existing commercial acetal copolymer blends; (d) preparing copolymers amenable to surface modifications; and (e) preparing crosslinked copolymers.

SUMMARY OF THE INVENTION

The present invention concerns the use of 5,6-epoxy-1-3-dioxepane as a comonomer in copolymerization reactions with trioxane to produce acetal copolymers of improved thermal stability containing oxirane functional groups. The oxirane functional group provides a highly reactive functional group useful for further modification or crosslinking.

The oxirane functional groups of the epoxidized acetal copolymers are further modified using a one step amination-hydrolysis process to produce acetal copolymers having amine-backbone functional groups. This one step amination-hydrolysis can also be used to modify 5,6-epoxy-1-3-dioxepane to produce aminated comonomers which may also be used in polymerization reactions. The oxirane functional groups of the copolymers can also be grafted with stabilizers such as polyamides or compatibilizers such as silicones.

The present invention also concerns methods for producing highly crosslinked epoxidized acetal copolymers of improved toughness and thermal stability. These methods comprise the copolymerization of 5,6-epoxy-1-3-dioxepane and trioxane using a high comonomer feed of 5,6-epoxy-1-3-dioxepane.

BRIEF DESCRIPTION OF THE FIGURES

FIG. 2 illustrates a proton-NMR spectrum of TX-EPDXPA copolymer in DMSO-$d_6$.

DETAILED DESCRIPTION OF THE INVENTION

EXAMPLE 1

Synthesis of monomers

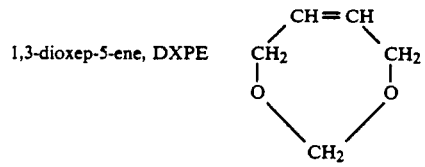

Figure 1:
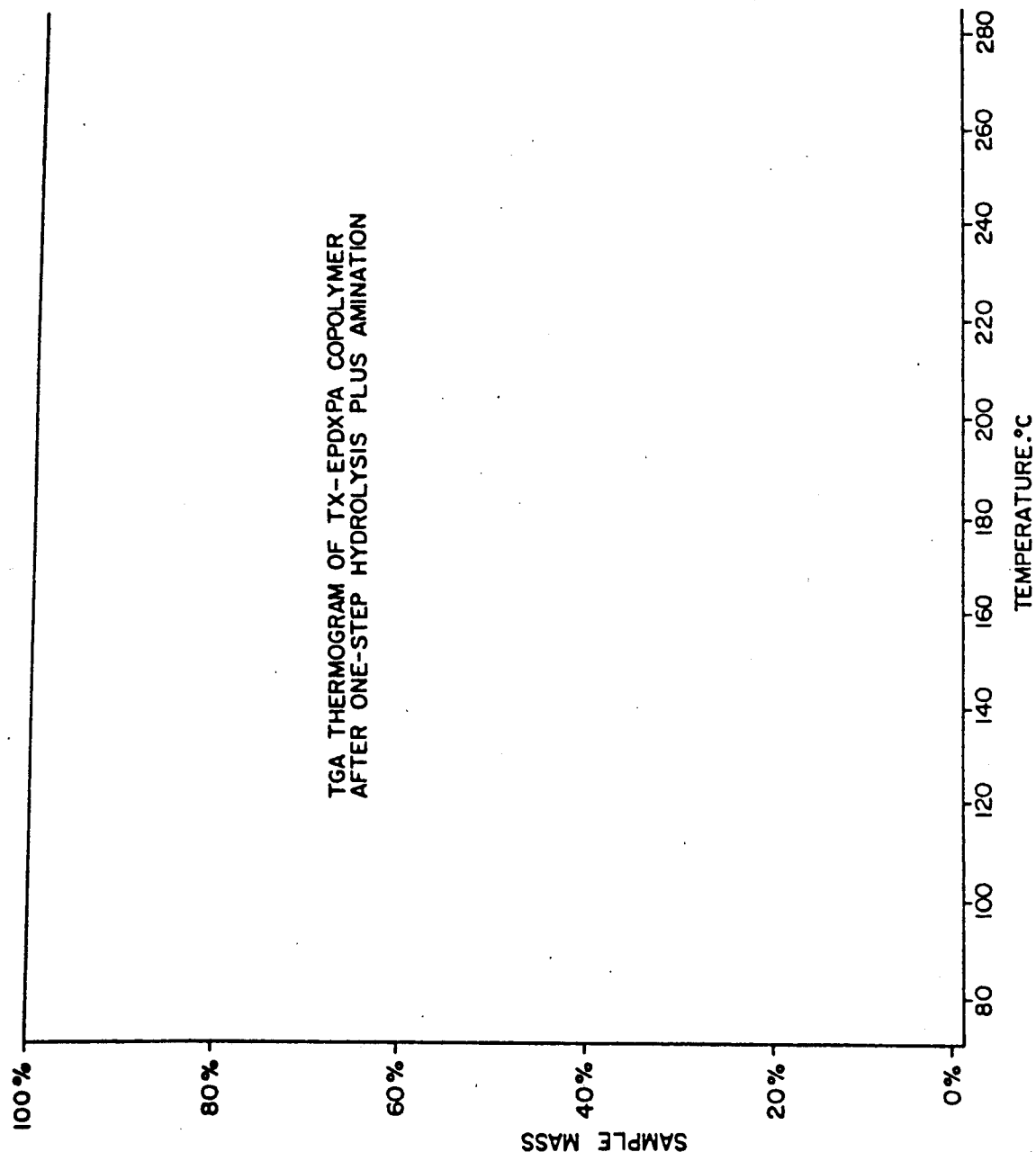
FIG. 1 illustrates a TGA Thermogram of TX-EPDXPA copolymer after one-step hydrolysis plus amination.

A mixture of 176 g. (2 moles) of cis-2-butene-1,4-diol, 60 g (2 moles) of paraformaldehyde, 25 ml. of benzene and 0.25 g. of p-toluenesulfonic acid was refluxed under a Dean-Stark trap until the removal of water was completed. Distillation of the reaction mixture after the removal of benzene yielded 172 g. of crude 1,3-dioxep-5-ene (b.p. 120°–126° C.). The crude product containing small amounts of water and formaldehyde was purified by redistillation from solid potassium hydroxide. Pure 1,3-dioxep-5-ene (b.p. =130° C.) was obtained in the amount of 160 g.

EXAMPLE 2

Copolymerization of Trioxane with 1,3-Dioxeo-5-ene

In a dry flask (Kjeldahl, 100 ml) were placed 28.5 g of trioxane and 1.5 g of 1,3-dioxep-5-ene. The flask was capped with a serum stopper. After removing the air and the dissolved gas under vacuum from the reaction mixture, the flask was flushed with nitrogen. The contents were melted and mixed together at a temperature range of 60° to 65° C. with a magnetic stirrer in an oil bath. Then, 0.05 ml of boron trifluoride etherate was injected through the serum stopper into the flask kept in an oil bath at 60° C. The color of the solution immediately became dark brown. Within about several minutes the solution became immobilized by the growth of the polymer throughout the flask. The polymerization was allowed to proceed at 60° C. for 20 hours. At the conclusion of polymerization, the polymer was removed and ground into small chunks. The crude polymer was washed with 60 ml of a methanol solution with 5% triethanolamine and then collected by filtration. The product was about 24 gms. The unstable end groups were removed by base hydrolysis in the following procedure.

Into a 500 ml, two-necked round bottom flask fitted with an air-cooled, straight through condenser, thermometer and magnetic stirrer were placed crude polymer (24 g), DMF (120 ml), Benzyl alcohol (120 ml) and 1% TEA (of total solution volume). The mixture was stirred and heated at 160°–170° C. to dissolve the solids. The contents were maintained at refluxing condition until visible evolution of formaldehyde stopped. The polymer solution was cooled down to precipitate out solid material. The solid was removed and washed by acetone three times. The polymer was filtered and dried under vacuum at 40° C. The yield was about 18 gms.

EXAMPLE 3

Epoxidation OF TX-DXPE

A dry 100 ml. three neck round bottom flask (with magnetic stirrer) was charged with 0.6 g. TX-DXPE copolymer in 40 ml. DMF. The contents were heated to 130° C. in order to dissolve the solid. The polymer solution gelled after cooling in an ice bath. 3-Chloroperoxybenzoic acid (0.1 g.) dissolved in DMF (20 ml.) was then introduced into the gelled mixture. The reaction was carried out under nitrogen at 0°–5° C. for 6 hours. A milkywhite precipitate (n-chlorobenzoic acid) began to separate from the reaction solution after about 30 minutes. The reaction was allowed to proceed overnight at room temperature and then again cooled. The cooled mixture was poured into 100 ml. H₂O. The polymer was suspended at the top of the solution. The polymer was then filtered off and washed once with 5% aqueous sodium bicarbonate (100 ml.) and three times with hot water. The polymer was dried at 40° C. under vacuum. The yield was 0.5 gms.

EXAMPLE 4

5,6-epoxy-1,3-dioxeoane, EPDXA

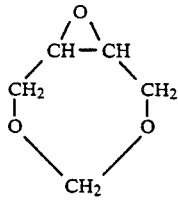

A dry one liter, three neck round bottom flask (with magnetic stirrer) was charged with 29.6 g. (0.14 mole) of 3-chloroperoxybenzoic acid and 475 ml. methylene chloride. The vessel was cooled to 0°–5° C. in an ice bath. A solution of 1.3 dioxep-5-ene (FW 100, bp 130° C.), 14.3 grams in 75 ml. methylene chloride, was added dropwise under nitrogen atmosphere. The temperature in the flask was maintained at 0°–5° C. during the addition and for four hours thereafter. The reaction was allowed to proceed overnight at room temperature and was then refluxed for an additional 4 hours.

A milky white precipitate (3-chlorobenzoic acid) began to separate from the reaction solution as the vessel was being cooled. The white precipitate was filtered out and the solution washed once with 5% aqueous sodium bicarbonate (300 ml.) and 3 times with water. The organic solvent layer was separated and dried with magnesium sulfate. After the solvent (CH₂Cl₂) was completely evaporated with a rotary evaporator, a white product was obtained (m.p. 54° C.).

EXAMPLE 5

Amination of 5,6-epoxy-1,3-dioxeoane

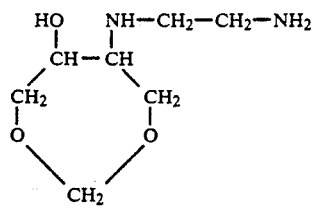

5,6-epoxy-1,3-dioxepane (EPDXPA) 0.58 g. (FW 116, 0.005 mole) and 0.55 ml. of diethylene-triamine were dissolved in 30 ml. of methanol. The mixture was refluxed at 75° C. for 5 hours. The solvent was removed by a rotary evaporator and the unreacted amine was separated under vacuum at 100° C. The product was a brown gummy material. The same procedure was carried out for aminations with diethylamine, ethylenediamine and tetraethylenepentamine.

EXAMPLE 6

Copolymerization of Trioxane with 5,6-epoxy-1,3 dioxepane

In a dry flask (Kjeldahl, 100 ml.) were placed 12.7 g. of trioxane and 1.41 g. (10%, of 5,6-epoxy-1,3-dioxepane). The flask was capped with a serum stopper. After removing the air and the dissolved gas under vacuum from the reaction mixture, the flask was flushed with nitrogen gas. The contents were melted and mixed together with a magnetic stirrer in an oil bath (60°–65° C.). Boron-trifluoride etherate (0.05 ml.) was then injected through the serum stopper into the flask. The color of the solution changed from brown to white. Within about fifteen minutes the solution became immobilized due to the growth of the polymer throughout the flask. The reaction was allowed to proceed at 60° C. for 20 hours. At the conclusion of polymerization, the TX-EPDXPA polymer was removed and ground into small chunks. The crude polymer (6.9 gm.) was washed once with 40 ml. solution of 5% triethanolamine in methanol and then three times with methanol. The copolymer was dried under vacuum at 40° C.

The incorporation of epoxide group through the copolymerization of trioxane with EPDXPA was substantiated by the 3.3 ppm proton absorption in proton NMR spectra and the 57 5 ppm absorption in C¹³ NMR spectra.

When this copolymerization reaction was carried out with a high EPDXPA comonomer feed, e.g. 16% feed, a crosslinked copolymer with extreme toughness was produced.

Homopolymerizations of EPDXPA may also be performed.

The amine-modified EPDXPA comonomers described above may also be used in copolymerizations with trioxane to produce acetal copolymers with backbone acetal groups.

EXAMPLE 7

One-step Hydrolysis and Amination of Epoxidized Copolymer

The epoxide group in the polymer chain provides a reactive site for further modification. This example demonstrates that the amination of the epoxide group can take place while the copolymerization product of Example 6 is being hydrolyzed to remove its unstable end groups.

Into a 250 ml., two necked flask fitted with a air cooled condenser and a thermometer were placed 4 g. epoxidized copolymer, DMF (40 ml.), benzyl alcohol (20 ml.) and 0.9 ml. diethylenetriamine. The mixture was stirred by means of a magnetic stirrer and refluxed at 170° C. for 30 minutes. Refluxing conditions were maintained until visible evolution of formaldehyde stopped. The reaction mixture changed in color from yellow to brown. The solution was cooled in order to precipitate solid material. The solid was then filtered and washed three times with acetone. The polymer was filtered and dried at 40° C. under vacuum. The yield was 2.6 gms.

When the TX-EPDXPA copolymer of this invention was aminated in the one-step hydrolysis plus amination process a copolymer of unusually high thermal stability was produced.

A Carbon 13 NMR spectrum of a sample from such a one step procedure evidenced the amination of the TX-EPDXPA copolymer. The TGA thermogram of such an animated polymer shows superior thermal stability to that of commercially available trioxane-ethylene oxide polymer. (FIG. 1).

EXAMPLE 8

Amination of TX-EPDXPA

Into a 50 ml round bottom flask fitted with an air cooled condenser were placed 1 g of copolymer (TX EPDXPA 1% incorporation) and 10 ml DMF. The polymer was dissolved in the solvent by heating at 150° C. Phenethylamine (1 ml) was then added directly and the mixture was stirred at 150° C. for 2 hours. The reaction mixture gradually became a brown solution. The solution was cooled to precipitate solid material. The aminated polymer was then filtered and washed three times with acetone. The polymer was filtered and dried at 40° C. under vacuum.

Reaction of TX-EPDXPA with dodecylamine was also performed.

Proton NMR spectrum of the product of the reaction of the epoxy copolymer with dodecylamine indicated that some of the amine reacted with the backbone epoxy-groups even though most of the epoxy groups remained unreacted. Only a low level of the (—CH$_2$—)$_{10}$ group was found, indicating the low reactivity of back bone epoxy functional groups.

EXAMPLE 9

Grafting with Polydimethylsiloxanes

The epoxy functional groups of TX-EPDXPA can be grafted with other functional molecules such as compatibilizers. This example demonstrates the grafting of a polysiloxane compatibilizer. Aminopropyldimethyl terminated polydimethylsiloxane was from Petrarch System, Inc., Cat. No. PS513 ("PS513"). In a 50 ml flask equipped with a magnetic stirrer and reflux condenser were placed copolymer (1 g Tx -EPDXPA). DMF (10 ml) and PS 513 (1 ml). The mixture was stirred and refluxed at 160° C. for about 2 hours. The polymer solution was cooled to precipitate out solid material. The solid was washed with toluene and at 100° C. with acetone at room temperature. The polymer was filtered and dried under vacuum at 40° C. The yield was 0.85 gms.

A proton NMR spectrum of the grafting product of the reaction of amine-terminated polysiloxane shows an absorption peak at 0.0ppm due to the methyl protons of the dimethylsiloxane group. A 1.6% incorporation of the amine terminated polysiloxane was found. The reactivity of epoxide ring on the backbone may be lower than that of pendant epoxide due to steric effect. The reaction time tried was 2 hours. Longer reaction time may lead to better yield. Siloxane polymers have only limited solubility in DMF. The reaction of TX-EPDXPA with an amine terminated silicone leads to a more hydrophobic polymer.

EXAMPLE 10

Grafting with Polyamide Stablizer

In this example grafting of the TX-EPDXPA with a polyamide stablizer is demonstrated. The stablizer used was Elvamide ®-8066 which is a short chain polyamide dispersion stabilizer.

In a 50 ml flask equipped with a magnetic stirrer and air-cooled straight condenser were placed copolymer (0.6 g TX EPDXPA). DMF (10 ml) and Elvamide 8066 (0.2 g). The copolymer was dissolved in the solvent by heating at 140° C. The reaction mixture was stirred at 140° C. for 2 hrs. The polymer solution was cooled to precipitate out solid material. The solid was washed with o-chlorophenol. The polymer was then filtered and washed once again with acetone. The polymer was filtered and dried at 40° C. under vacuum.

EXAMPLE 11

The mole percent epoxide incorporation into the acetal copolymers was derived from peak areas of the proton NMR spectrum as shown in FIG. 2 as follows:

$$\frac{\text{Epoxide}}{TX + \text{Epoxide}} \text{ mole \%} = \frac{E}{E + S/3} \times 100$$

The following table summarizes the feed of EPDXPA vs. incorporation of EPDXPA in mole percent for TX-EPDXPA:

TABLE 1

| Sample | Epoxide Mole % | |
|---|---|---|
| | Feed % EPDXPA | Incorporation % EPXDPA |
| #40 | 3.9 | 1.1 |
| #42 | 5.5 | 1.5 |
| #27 | 7.9 | 7.0 |

At 7.9% EPDXPA feed, a portion of the copolymer was not soluble. At 16% feed, a highly cross-linked copolymer with extreme toughness was produced.

The TX-EPDXPA copolymer was aminated with phenythylamine. Proton-NMR spectrum were performed which indicated an absorption peak at 1.2 ppm. due to the methylene protons of the amine; and a 7.2 ppm peak corresponding to the aromatic protons. For a copolymer with 1% epoxide in corporation, a 0.1% mole amination was obtained.

EXAMPLE 12

Crosslinking With Diamine or Diisocyanate

The TX-EPDXPA epoxy copolymer can be crosslinked with diamine or diisocyanate. The procedure for the crosslinking reaction is as follows: 1.5 g TX-EPDXPA copolymer was added to a test tube. The diamine or diisocyanate was then added and mixed well in the test tube. The mixture was heated to 190° C. in an oil bath for 20 min, and then dissolved in DMSO at 155° C. for 15 min. This step serves to remove the unreacted copolymer, which remains in solution under such conditions. The mixture was then hot filtered at 150° C. The insoluble crosslinked copolymer was then swollen with DMSO and placed in acetone overnight to remove the DMSO. The samples were filtered and washed with acetone again and dried under vacuum. The results of the crosslinking process are as follows:

TABLE II

| Crosslinker | Weight of Crosslinker | Weight of Copolymer | Gel % |
|---|---|---|---|
| $NH_2(CH_2)_{11}NH_2$ | 0.05 g (3%) | 1.5 g | 14 |
| $NH_2(CH_2)_{11}NH_2$ | 0.10 g (6%) | 1.5 g | 25 |
| Trimethyl-hexamethylene | 0.10 g (6%) | 1.5 g | 56 |

TABLE II-continued

| Crosslinker | Weight of Crosslinker | Weight of Copolymer | Gel % |
|---|---|---|---|
| diisocyanate | | | |

The diisocyanate crosslinking reagent is more reactive for the epoxy copolymer containing ca. 4% by weight epoxy group. A proton NMR spectrum of the filtrate from the diisocyanate crosslinking reaction, showed that a significant amount of the backbone epoxy group remained unreacted with the crosslinker.

What is claimed is:

1. A method for producing an acetal copolymer containing backbone-epoxide groups which comprises copolymerizing trioxane with 5,6-epoxy-1,3-dioxepane, wherein the comonomer feed of 5,6-epoxy-1,3 dioxepane is about 10% or less by weight of the combined total weight of the comonomers.

2. The copolymer produced by the method of claim 1.

* * * * *